US012673174B2

(12) United States Patent
    Aylsworth

(10) Patent No.:    US 12,673,174 B2
(45) Date of Patent:     Jul. 7, 2026

(54) METHODS AND SYSTEMS OF SUPPLYING THERAPEUTIC GAS

(71) Applicant: INCOBA, LLC, Chesterfield, MO (US)

(72) Inventor: Alonzo C. Aylsworth, Wildwood, MO (US)

(73) Assignee: Incoba, LLC, Chesterfield, MO (US)

( * ) Notice: Subject to any disclaimer, the term of this patent is extended or adjusted under 35 U.S.C. 154(b) by 1043 days.

(21) Appl. No.: 17/854,889

(22) Filed: Jun. 30, 2022

(65) Prior Publication Data

US 2024/0001058 A1     Jan. 4, 2024

(51) Int. Cl.
    *A61M 16/00*       (2006.01)
    *A61M 16/06*       (2006.01)
    *A61M 16/20*       (2006.01)

(52) U.S. Cl.
    CPC ...... *A61M 16/022* (2017.08); *A61M 16/0666* (2013.01); *A61M 16/202* (2014.02); *A61M 2016/0027* (2013.01); *A61M 2016/0036* (2013.01)

(58) Field of Classification Search
    CPC ............ A61M 16/022; A61M 16/0666; A61M 16/202; A61M 2016/0027; A61M 2016/0036; A61M 2016/0018; A61M 16/1005; A61M 16/204; A61M 2205/3334; A61M 2205/3344; A61M 16/024; A61M 16/0677
    See application file for complete search history.

(56) References Cited

U.S. PATENT DOCUMENTS

| | | | | |
|---|---|---|---|---|
| 5,074,299 A | * | 12/1991 | Dietz | ................ A61M 16/0677 |
| | | | | 128/204.26 |
| 6,595,212 B1 | * | 7/2003 | Arnott | ............... A61M 16/0006 |
| | | | | 128/204.23 |
| 10,953,172 B2 | | 3/2021 | Aylsworth et al. | |
| 2003/0140924 A1 | | 7/2003 | Aylsworth et al. | |
| 2004/0079359 A1 | | 4/2004 | Aylsworth et al. | |
| 2005/0005942 A1 | | 1/2005 | Aylsworth et al. | |
| 2005/0011523 A1 | | 1/2005 | Aylsworth et al. | |
| 2005/0092321 A1 | | 5/2005 | Aylsworth et al. | |
| 2005/0145248 A1 | | 7/2005 | Aylsworth et al. | |
| 2005/0257788 A1 | | 11/2005 | Aylsworth et al. | |
| 2005/0257794 A1 | | 11/2005 | Aylsworth et al. | |
| 2005/0261600 A1 | | 11/2005 | Aylsworth | |
| 2006/0005834 A1 | | 1/2006 | Aylsworth et al. | |
| 2006/0060198 A1 | | 3/2006 | Aylsworth et al. | |
| 2006/0157058 A1 | | 7/2006 | Aylsworth et al. | |
| 2006/0169281 A1 | | 8/2006 | Aylsworth et al. | |
| 2006/0174883 A1 | | 8/2006 | Aylsworth et al. | |
| 2006/0174885 A1 | | 8/2006 | Aylsworth et al. | |
| 2006/0174888 A1 | | 8/2006 | Aylsworth et al. | |
| 2006/0272643 A1 | | 12/2006 | Aylsworth et al. | |

(Continued)

*Primary Examiner* — Elliot S Ruddie
(74) *Attorney, Agent, or Firm* — Dickinson Wright PLLC; Mark E. Scott

(57) ABSTRACT

Supplying therapeutic gas. At least one example is a method of providing therapeutic gas to a patient, the method comprising: sensing a signal indicative of an exhalation airflow from the patient, the exhalation airflow is non-zero and an airflow rate trending toward zero; sensing, during the exhalation airflow, a change in the airflow rate prior to a contiguous inhalation; and delivering a bolus of therapeutic gas to the proximal end of nasal cannula responsive to the change in the airflow rate.

18 Claims, 9 Drawing Sheets

(56) References Cited

U.S. PATENT DOCUMENTS

| 2006/0283517 | A1 | 12/2006 | McCulloh et al. |
|---|---|---|---|
| 2007/0186929 | A1 | 8/2007 | Aylsworth et al. |
| 2007/0214955 | A1 | 9/2007 | Aylsworth et al. |
| 2007/0214960 | A1 | 9/2007 | Aylsworth et al. |
| 2007/0272239 | A1 | 11/2007 | Aylsworth et al. |
| 2007/0272240 | A1 | 11/2007 | Aylsworth et al. |
| 2007/0277824 | A1 | 12/2007 | Aylsworth et al. |
| 2008/0006271 | A1 | 1/2008 | Aylsworth et al. |
| 2008/0142011 | A1 | 6/2008 | Aylsworth et al. |
| 2009/0071330 | A1 | 3/2009 | Aylsworth et al. |
| 2010/0186741 | A1 | 7/2010 | Aylsworth et al. |
| 2011/0120461 | A1 | 5/2011 | Aylsworth et al. |
| 2012/0053481 | A1 | 3/2012 | Aylsworth |
| 2012/0065533 | A1 | 3/2012 | Carrillo, Jr. et al. |
| 2013/0012828 | A1 | 1/2013 | Aylsworth |
| 2013/0263850 | A1* | 10/2013 | Acker ................. A61M 16/202 |
| | | | 128/203.14 |
| 2021/0196910 | A1 | 7/2021 | Aylsworth et al. |
| 2022/0176059 | A1 | 6/2022 | Aylsworth |
| 2022/0265164 | A1 | 8/2022 | Aylsworth |

* cited by examiner

METHODS AND SYSTEMS OF SUPPLYING THERAPEUTIC GAS

CROSS-REFERENCE TO RELATED APPLICATIONS

None.

BACKGROUND

Patients with respiratory ailments may be required to breathe a therapeutic gas, such as oxygen. The therapeutic gas may be delivered to the patient from a therapeutic gas source by way of a nasal cannula. In some cases, therapeutic gas is delivered to a patient continuously. That is, in continuous delivery the therapeutic gas is supplied at a constant flow rate throughout the patient's entire breathing cycle (i.e., both inhalation and exhalation). In other cases, in order to reduce consumption of the therapeutic gas, the therapeutic gas may be delivered in a bolus mode at the beginning of each inhalation. The bolus delivery conserves therapeutic gas, and thus the devices that implement bolus delivery are sometimes referred to as conservers.

When delivering therapeutic gas in bolus form, the earlier the bolus is provided during the inhalation, the better. The theory is that early therapeutic gas delivered is more likely to travel into the lungs and contact the pulmonary alveolus. By contrast, therapeutic gas delivered late in the inhalation may not travel far enough into the lungs to be useful.

Any system or method that better detects the beginning of the inhalation, and thus earlier delivery of the bolus of therapeutic gas, would provide a competitive advantage in the marketplace.

SUMMARY

One example is a method of providing therapeutic gas to a patient, the method comprising: sensing a signal indicative of an exhalation airflow from the patient, the exhalation airflow is non-zero and an airflow rate trending toward zero; sensing, during the exhalation airflow, a change in the airflow rate prior to a contiguous inhalation; and delivering a bolus of therapeutic gas to a proximal end of nasal cannula responsive to the change in the airflow rate.

In the example method, sensing the signal indicative of the exhalation airflow may further comprise sensing air pressure over time, the air pressure over time indicative of the exhalation airflow.

In the example method, sensing the change in the airflow rate may further comprise sensing a decrease in the airflow rate.

In the example method: sensing the signal indicative of the exhalation airflow may further comprise receiving a responsive AC signal from a diaphragm of a diaphragm sensor, the diaphragm of the diaphragm sensor abutting a platform that limits movement of the diaphragm during at least a portion of the exhalation airflow; and sensing the change in the airflow rate may further comprise sensing a change in magnitude of an envelope defined by the responsive AC signal from the diaphragm sensor. Sensing the change in magnitude of the envelope defined by the responsive AC signal from the diaphragm sensor may further comprise sensing a change in magnitude of an envelope defined by peaks of the responsive AC signal. Delivering the bolus of therapeutic gas may further comprise delivering the bolus of therapeutic gas responsive to the envelope having a magnitude rising through a trigger reference.

Another example is a therapeutic gas delivery device comprising: a controller; a first sensor electrically coupled to the controller and fluidly coupled to a first-hose connection, the first sensor configured to create a first signal indicative of airflow through the first-hose connection; and a first valve electrically coupled to the controller and configured to fluidly coupled a source-hose connection to the first-hose connection. The controller may be: sense, by way of the first signal indicative of airflow, exhalation airflow associated with the first-hose connection, the exhalation airflow having an airflow rate, and the airflow rate trending toward zero at a waning rate; sense, during the exhalation airflow, a change in the waning rate, the change prior to a contiguous inhalation; and command the first valve to couple the source-hose connection to the first-hose connection to deliver a bolus of therapeutic gas, the command responsive to the change in the waning rate.

The example device may further comprise: a second sensor electrically coupled to the controller and fluidly coupled to a second-hose connection, the second sensor configured to create a second signal indicative of airflow of through the second-hose connection; a second valve electrically coupled to the controller and configured to fluidly couple the source-hose connection to the second-hose connection; and when the controller senses exhalation airflow, the controller may be further configured to sense by way of the first signal indicative of airflow and the second signal indicative of airflow. The controller may be further configured to command the second valve to couple the source-hose connection to the second-hose connection responsive to the change in the waning rate.

In the example device, the first sensor may further comprise a first pressure sensor associated with the first-hose connection.

In the example device: the first sensor may further comprise a diaphragm sensor comprising a diaphragm; the controller may be further configured to receive a responsive AC signal from the diaphragm of the diaphragm sensor, the diaphragm abutting a platform that limits movement of the diaphragm in an exhalation direction for at least a portion of the exhalation; and when the controller senses the change in the waning rate, the controller may be further configured to sense the change in magnitude of an envelope defined by the responsive AC signal from the diaphragm sensor. When the controller senses the change in magnitude of the envelope defined by the ΔC responsive signal from the diaphragm sensor, the controller may be further configured to sense the change in magnitude of the envelope defined by peaks of the ΔC responsive signal from the diaphragm sensor. When the controller commands the first valve to deliver the bolus of therapeutic gas, the controller may be further configured to deliver the bolus of therapeutic gas responsive to the envelope having a magnitude rising through a trigger reference.

Yet another example is a therapeutic gas delivery device comprising: a controller; a first sensor electrically coupled to the controller and fluidly coupled to a first-hose connection, the first sensor configured to create a first signal indicative of airflow associated with the first-hose connection; a first valve electrically coupled to the controller and configured to fluidly coupled a source-hose connection to the first-hose connection; a second sensor electrically coupled to the controller and fluidly coupled to a second-hose connection, the second sensor configured to create a second signal indicative of airflow of associated with the second-hose connection; and a second valve electrically coupled to the controller and configured to fluidly couple the source-hose connection to the second-hose connection. The controller may be configured to: read the first signal indicative of airflow; read the second signal indicative of airflow; sense, based on the reading, exhalation associated with the first-hose connection or the second-hose connection, the exhalation having an airflow rate, and the airflow rate declining over time; sense, during the exhalation, an increase in the airflow rate, the increase in the airflow rate prior to a contiguous inhalation; and command the first valve to couple the source-hose connection to the first-hose connection to deliver a bolus of therapeutic gas, the command responsive to the increase in the airflow rate.

In the therapeutic gas delivery device, the controller may be further configured to command the second valve to couple the source-hose connection to the second-hose connection responsive to the increase in airflow rate.

In the therapeutic gas delivery device: the first sensor may further comprise a first pressure sensor associated with the first-hose connection; and the second sensor may further comprise a second pressure sensor associated with the second-hose connection.

In the therapeutic gas delivery device: the first sensor may further comprise a diaphragm sensor comprising a diaphragm; when the controller reads the first signal indicative of airflow, the controller may be further configured to receive a responsive AC signal from the diaphragm of the diaphragm sensor; and when the controller senses the increase in the airflow rate, the controller may be further configured to sense a change in magnitude of an envelope defined by the responsive AC signal from the diaphragm sensor.

In the therapeutic gas delivery device, when the controller senses the change in magnitude of the envelope defined by the responsive AC signal from the diaphragm sensor, the controller may be further configured to sense the change in magnitude of the envelope defined by peaks of the responsive AC signal from the diaphragm sensor.

BRIEF DESCRIPTION OF THE DRAWINGS

For a detailed description of example embodiments, reference will now be made to the accompanying drawings in which.

DEFINITIONS

Figure 1:
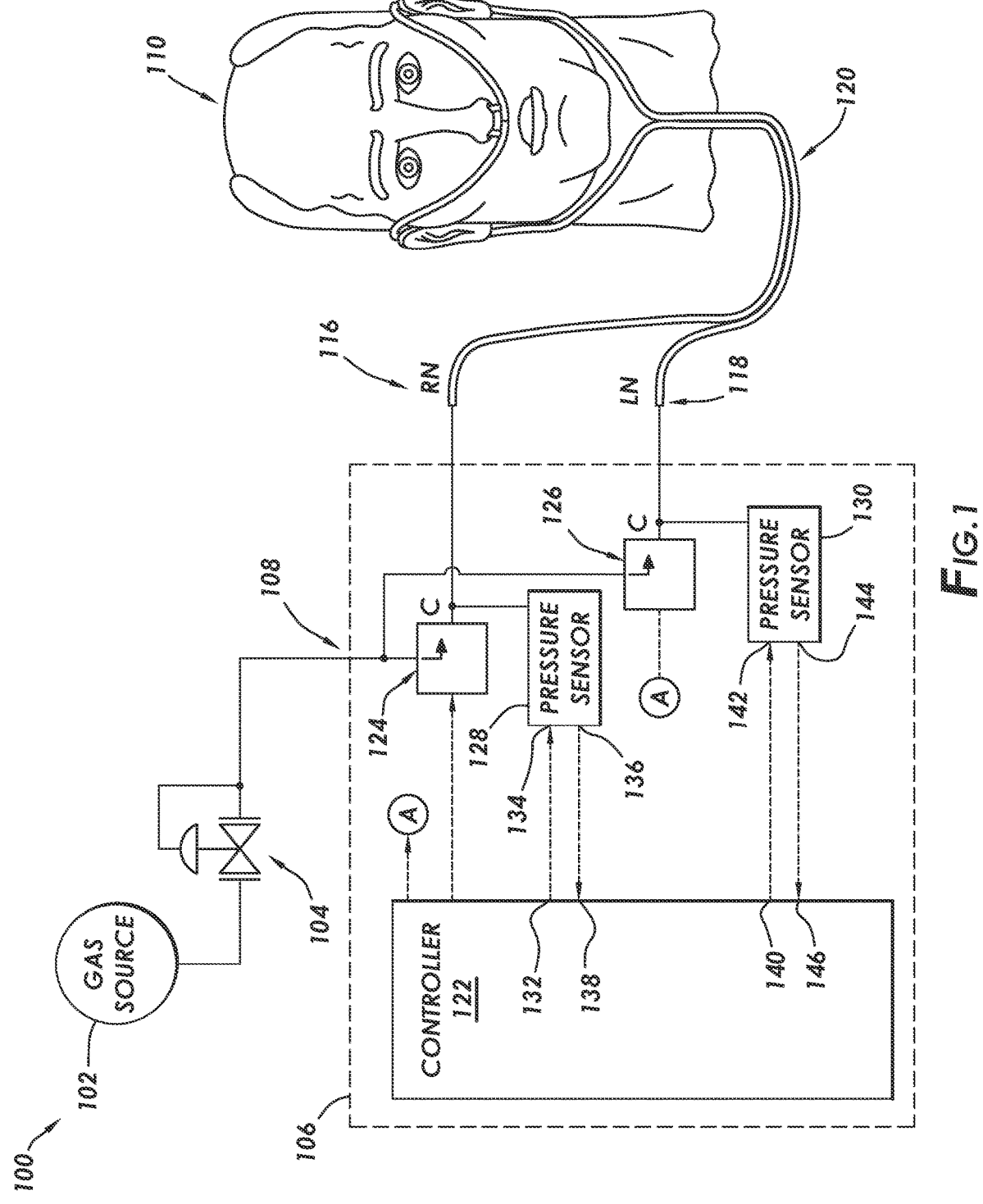
FIG. 1 shows a system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"About," in reference to a recited value, shall mean the recited value plus or minus+/− ten percent (10%).

"As s e rt" shall mean changing the state of a Boolean signal. Boolean signals may be asserted high or with a higher voltage, and Boolean signals may be asserted low or with a lower voltage, at the discretion of the circuit designer. Similarly, "de-assert" shall mean changing the state of the Boolean signal to a voltage level opposite the asserted state.

"AC" shall mean alternating current.

"DC" shall mean direct current.

"Nares" shall mean the nostrils of a patient.

"Naris" shall mean a single nostril of a patient, and is the singular of "nares."

"Controller" shall mean, alone or in combination, individual circuit components, an application specific integrated circuit (ASIC), a microcontroller with controlling software, a digital signal processor (DSP), a processor with controlling software, a programmable logic device (PLD), a field programmable gate array (FPGA), or a programmable system-on-a-chop (PSOC), configured to read inputs and drive outputs responsive to the inputs.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Many patients are provided therapeutic gas to address respiratory ailments, such as chronic obstructive pulmonary disease (COPD), pulmonary fibrosis, or oxygen desaturation issues associated with illness (e.g., SARS-CoV-19) or sleep disorders (e.g., central or obstructive sleep apnea). In situations where the supply of therapeutic gas is effectively limitless (e.g., hospitals), patients may be provided therapeutic gas continuously. In particular, the patient may wear a nasal cannula that has prongs or outlet ports that are associated, one each, with the nares of the patient. The therapeutic gas may flow continuously to both nares at a predetermined flow rate (e.g., 3 liters per minute (LPM)).

Regardless of whether the patient is inhaling or exhaling, the therapeutic gas continuously flows, and thus delivery by this method is referred to as "continuous flow."

A similar situation may exist for non-ambulatory patients in the home environment, where the therapeutic gas is provided from an oxygen concentrator. In the home environment with an oxygen concentrator, and regardless of whether the patient is inhaling or exhaling, the therapeutic gas may continuously flow.

However, in other situations the supply of therapeutic gas is limited, and thus additional devices and methods may be implemented to reduce therapeutic gas consumption. For ambulatory patients, a small portable gas cylinder may be used to provide the therapeutic gas. While theoretically possible to have the therapeutic gas flow continuously with a small portable gas cylinder, such makes the therapeutic gas available only for a short period of time. For that reason, related-art systems include conservers to extend the time the patient may use the small portable gas cylinder by providing a short burst or bolus of therapeutic gas at the beginning of each inhalation (e.g., during the first 100 milliseconds (ms) of the inhalation). More particularly still, gas cylinders, even when low, may have several hundred pounds of pressure. The bolus of therapeutic gas delivered by a conserver thus has relatively high pressure (e.g., 20 pounds per square inch (PSIG) or more) which provides a high velocity burst to help force the bolus into the lungs of the patient.

The volume of therapeutic gas delivered by a conserver is selected by a clinician during patient titration. In many cases, the patient is titrated with a continuous flow of therapeutic gas, and when the patient uses a system with a conserver the volume of therapeutic gas provided by each bolus is controlled or set using a known relationship between continuous flow prescription flow rate and conserve-mode volume. In particular, in situations where the patient is titrated using continuous flow, in the conserve mode the patient may be provided, at each inhalation, 16.5 milliliters (mL) of volume for every 1 LPM of continuous flow prescription flow rate.

Various examples are directed to methods and systems of providing therapeutic gas to a patient. More particularly, example systems sense exhalation airflow from the patient as part of the breathing cycle, and in particular sense (directly or indirect) a change in the exhalation airflow rate. That is, during periods of time when patient is exhaling, the rate of exhalation airflow changes over time. Near the end of the exhalation the airflow rate is non-zero and trending toward zero, and may be considered to exponentially or asymptotically approach zero. However, various examples detect a change in the airflow rate (e.g., a change from the exponential decay rate). The inventor of the current specification discovered that the change in the exhalation airflow rate is indicative of an upcoming inhalation, and thus example methods and systems deliver a bolus of therapeutic gas to the proximal end of the nasal cannula responsive to the change in the airflow rate. The therapeutic gas may thus be delivered earlier in the inhalation than systems that trigger bolus delivery based on airflow during inhalation. The specification now turns to an example system.

FIG. 1 shows a system 100 in accordance with at least some embodiments. The example system 100 comprises gas source 102. The gas source 102 may take any suitable form, such as a therapeutic gas cylinder. Because the pressure within the example therapeutic gas cylinder may be from several hundred pounds PSIG to several thousand PSIG, the gas source 102 may be associated with a pressure regulator 104. The pressure regulator 104 reduces the pressure of the therapeutic gas provided to the delivery system (discussed more below) to below 30 PSIG, in some cases to 25 PSIG and below, and in example cases between and including 20 PSI and 25 PSIG.

The therapeutic gas downstream of the pressure regulator 104 is fluidly coupled to a therapeutic gas delivery device or conserver 106. The example conserver 106 defines a source-hose connection 108 fluidly coupled to the pressure regulator 104 and the gas source 102. The example conserver 106 also defines a first-hose or right-naris hose connection 116 and a second-hose or left-naris hose connection 118. In example systems, the conserver 106 is fluidly coupled to a patient 110 by way of a dual-lumen or bifurcated nasal cannula 120. In particular, the example bifurcated nasal cannula 120 defines a hose or tube associated with the right naris, and a separate and distinct hose or tube associated with the left naris. The proximal end of the tube associated with the right naris is fluidly coupled to the right-naris hose connection 116. The proximal end of the tube associated with the left naris is fluidly coupled to the left-naris hose connection 118. Each tube has an associated nasal prong that, in use, is disposed in operational relationship with their respective naris.

Still referring to FIG. 1, and turning now to the conserver 106, in various examples the conserver 106 comprises both electrical components and mechanical or fluidic connections (e.g., with therapeutic gas considered a fluid). In order to differentiate between electrical connections and fluidic connections, FIG. 1 illustrates electrical connections between components with dashed lines, and fluidic connections (e.g., tubing connections between devices) with solid lines. The example conserver 106 of FIG. 1 comprises a controller 122. The example controller 122 may drive on/off or Boolean signals, such as signals to control the state of various electrically-controlled valves. Moreover, the example controller 122 may read signals (e.g., from various sensors) indicative of inhalations and exhalations through the breathing orifices of the patient 110.

The example conserver 106 comprises electrically-controlled valves in the example form of two-port valve 124 and two-port valve 126. Each of these two-port valves may be a five-volt solenoid operated valve that selectively couples an inlet port to an outlet or common port (each common port labeled as C in the figure). Two-port valves 124 and 126 may each be a part number R434007035, 5 Volt, 1.3 Watt, solenoid operated valve available from Aventics of Laatzen, Germany, or equivalents.

The inlet port of the two-port valve 124 is fluidly coupled to the source-hose connection 108, and thus the pressure regulator 104 and gas source 102. The common port of the two-port valve 124 is fluidly coupled to the right-naris hose connection 116, and thus the right naris of the patient 110, by way of the bifurcated nasal cannula 120. Similarly, the inlet port of the two-port valve 126 is fluidly coupled to the source-hose connection 108. The common port of the two-port valve 126 is fluidly coupled to the left-naris hose connection 118, and thus the left naris of the patient 110, by way of the bifurcated nasal cannula 120. The example two-port valves 124 and 126 may be normally open valves such that, in the absence of power, the conserver 106 defaults to continuous flow. In other cases, such as cases in which there is an alternate mechanism to provide continuous flow in the event of failure, the two-port valves 124 and 126 may be normally-closed valves to preserve battery power of the conserver 106.

Each two-port valve 124 and 126 is electrically coupled to the controller 122. By selectively applying voltage from the controller 122 on respective electrical connections, the controller 122 may be able to control the flow state of conserver 106. For example, the two-port valve 124 may selectively couple therapeutic gas from the gas source 102 and the pressure regulator 104 to the common port and therefore to the example right naris. Likewise, the two-port valve 126 may selectively couple therapeutic gas from gas source 102 and the pressure regulator 104 to the common port and therefore the example left naris.

The example conserver 106 further comprises pressure sensors 128 and 130.
The example pressure sensor 128 is fluidly coupled to the right-naris hose connection 116 downstream of the two-port valve 124 (i.e., between the two-port valve 124 and the right-naris hose connection 116). Thus, the pressure sensor 128 measures pressure associated with airflow during portions of the breathing cycle of the patient 110. Moreover, given the location of the fluidic connection of the pressure sensor 128 to the right-naris hose connection 116, the pressure sensor 128 may also measure pressure of the therapeutic gas during bolus delivery to the right naris. The example pressure sensor 130 is fluidly coupled to the left-naris hose connection 118 downstream of the two-port valve 126 (i.e., between the two-port valve 126 and the left-naris hose connection 118). Thus, the pressure sensor 130 measures pressure associated with airflow during portions of the breathing cycle of the patient 110. Moreover, given the location of the fluidic connection of the pressure sensor 130 to the left-naris hose connection 118, the pressure sensor 130 may also measure pressure of the therapeutic gas during bolus delivery to the left naris.

As the patient inhales, outlet ports of the nasal cannula 120 disposed proximate to the openings of each naris experience a pressure drop. The pressure drop may be sensed through the nasal cannula 120 and associated tubing by each of the pressure sensors 128 and 130. Likewise as the patient exhales, the outlet ports of the nasal cannula 120 disposed proximate to the openings of each naris experience a pressure increase. The pressure increase may be sensed through the nasal cannula 120 and associated tubing by each of the pressure sensors 128 and 130.

The example pressure sensors 128 and 130 are electrically coupled to the controller 122 such that the controller 122 can read the pressure sensed by each sensor. Each pressure sensor is designed and constructed to create a signal indicative of airflow through their respective hose connections. In the example system, the pressure sensor 128 is a diaphragm sensor comprising a diagraph having a first side fluidly coupled to the right-naris hose connection 116, and a second side exposed to atmospheric pressure. The diaphragm flexes or bends toward the atmospheric side during exhalation and bolus delivery (e.g., when the pressure at the right-naris hose connection 116 is higher than atmospheric pressure). The diaphragm flexes or bends away from the atmospheric side during inhalation (e.g., when the pressure at the right-naris hose connection 116 is lower than atmospheric pressure). In order to read the pressure sensed by the pressure sensor 128, the controller 122 provides an interrogating AC signal from a signal output 132 of the controller 122 to a signal input 134 of the pressure sensor 128. The signal input 134 is electrically coupled to a metallized side of the diaphragm (e.g., the atmospheric side). The example pressure sensor 128 defines a sense output 136 upon which a responsive AC signal is detected and provided to the controller 122 by way of the sense input 138. The responsive AC signal provided to the sense output 136 and sense input 138 has a magnitude proportional the relative location of the diaphragm.

Similarly, the pressure sensor 130 is a diaphragm sensor comprising a diaphragm having a first side fluidly coupled to the left-naris hose connection 118, and a second side exposed to atmospheric pressure. The diaphragm of the pressure sensor 130 flexes or bends toward the atmospheric side during exhalation and bolus delivery (e.g., when the pressure at the left-naris hose connection 118 is higher than atmospheric pressure). And the diaphragm flexes or bends away from the atmospheric side during inhalation (e.g., when the pressure at the left-naris hose connection 118 is lower than atmospheric pressure). In order to read the pressure sensed by the pressure sensor 130, the controller 122 provides an interrogating AC signal from signal output 140 of the controller 122 to the signal input 142 of the pressure sensor 130. The signal input 142 is electrically coupled to a metallized side of the diaphragm of the pressure sensor 130 (e.g., the atmospheric side). The example pressure sensor 130 defines a sense output 144 upon which a responsive AC signal is detected and provided to the controller 122 by way of the sense input 146. The responsive AC signal provided to the sense output 144 and sense input 146 has a magnitude proportional the relative location of the diaphragm. Example pressure sensors are discussed in greater detail below.

In other examples, the pressure sensors 128 and 130 may be fluidly coupled to the ports of the valves implemented as three-port valves. In such cases, the pressure sensors 128 and 130 may be fluidly coupled to their respective hose connections at all times except when the respective valves change positions to provide a bolus of therapeutic gas. Regardless of the precise fluidic connections of the pressure sensors 128 and 130, the controller 122 may be able to read an indication of when the patient 110 is inhaling, and read an indication of when the patient 110 is exhaling.

Figure 2:
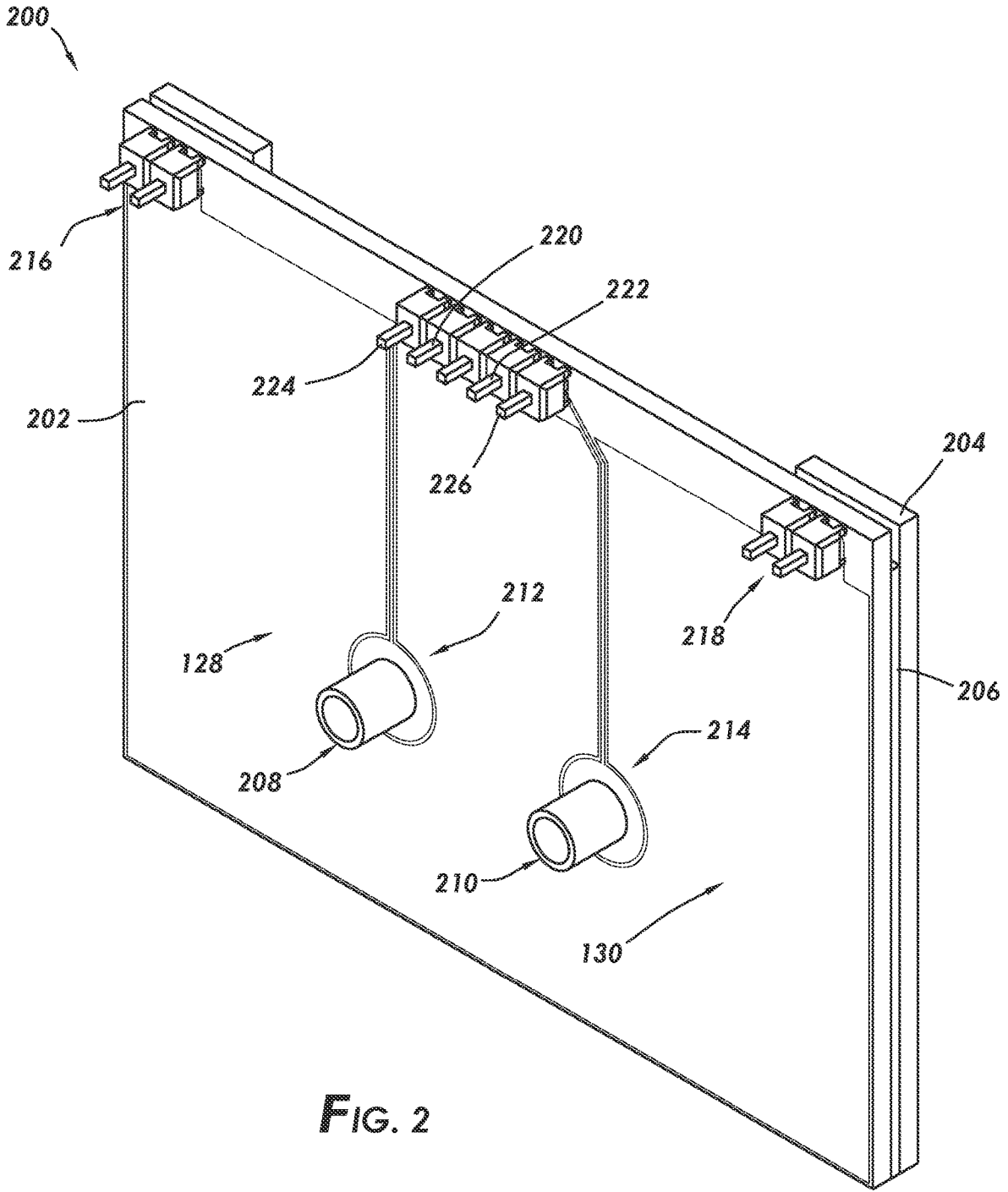
FIG. 2 shows a front perspective view of printed circuit board (PCB) assembly that implements the example pressure sensor, in accordance with at least some embodiments.

FIG. 2 shows a front perspective view of printed circuit board (PCB) assembly 200 (hereafter PCB assembly 200) that implements the example pressure sensors 128 and 130. In particular, the PCB assembly 200 comprises a patient-side or front PCB 202, an atmospheric-side or back PCB 204, and a spacer assembly 206 disposed between and abutting the inside surfaces of the front PCB 202 and the back PCB 204. In example cases, the spacer assembly 206 implements the diaphragms (not visible) of the pressure sensors 128 and 130. Disposed on the front PCB 202 is a right-naris port 208 fluidly coupled to an internal volume defined between the front PCB 202 and a patient side of the diaphragm of pressure sensor 128. When assembled within the conserver 106 (FIG. 1), the right-naris port 208 is fluidly coupled to the right-naris hose connection 116. Further disposed on the front PCB 202 is a left-naris port 210 fluidly coupled to an internal volume defined between the front PCB 202 and a patient side of the diaphragm of the pressure sensor 130. When assembled within the conserver 106, the left-naris port 210 is fluidly coupled to the left-naris hose connection 118.

Surrounding the right-naris port 208 is an electrical trace defining an antenna 212 (e.g., a loop antenna) associated with the pressure sensor 128. Similarly, surrounding the left-naris port 210 is an electrical trace defining an antenna 214 (e.g., a loop antenna) associated with the pressure sensor 130. While the example the antennas 212 and 214 surround their respective ports 208 and 210, in other cases the antennas may be placed at any suitable location relative to the respective diaphragms, and not necessarily circumscribing the respective ports 208 and 210. The front PCB 202 further defines a plurality of electrical connectors or electrical pins. The set of electrical pins 216 and the set of electrical pins 218 define connections to various shielding. In the example of FIG. 2, electrical pin 220 is electrically coupled to the antenna 212, and electrical pin 222 is electrically coupled to the antenna 214. Electrical pin 224 is electrically coupled to the metallized side of the diaphragm of pressure sensor 128, and electrical pin 226 is electrically coupled to the metallized side of the diaphragm of pressure sensor 130. Other pinouts and other electrical connections (e.g., female connectors) are possible, and thus the arrangement of FIG. 2 shall not be read as a limitation. In example systems, the interrogating AC signal is fed to the electrical pins 224 and 226, and the responsive AC signals are sensed by the antennas 212 and 214 and provided to electrical pins 220 and 222, respectively.

Figure 3:
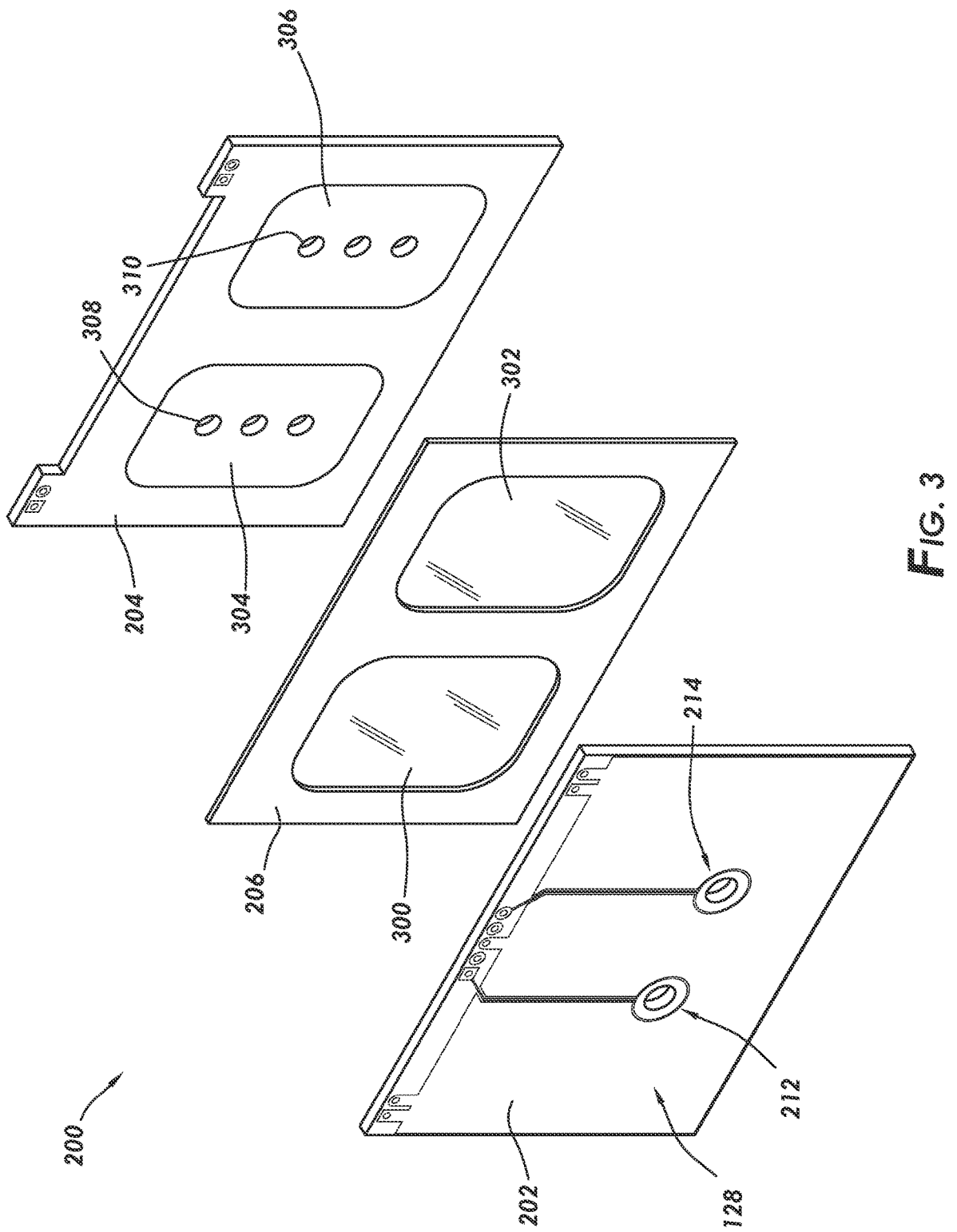
FIG. 3 shows an exploded perspective view of the PCB assembly in accordance with at least some embodiments.

FIG. 3 shows an exploded perspective view of the PCB assembly 200. In particular, FIG. 3 shows the front PCB 202, the back PCB 204, and the spacer assembly 206 in greater detail. Several components are omitted from FIG. 3 (e.g., electrical pins, ports) so as not to unduly complicate the figure. The example spacer assembly 206 defines a diaphragm 300 associated with pressure sensor 128 and a diaphragm 302 associated with pressure sensor 130. The example diaphragms 300 and 302 (e.g., polyester film metallized on one side) are disposed within the spacer assembly 206 such that, depending on the differential pressure applied, the diaphragms 300 and 302 may move or flex toward or away from the antennas 212 and 214, respectively.

The example back PCB 204 defines a first area 304 associated with the diaphragm 300, and a second area 306 associated with the diaphragm 302. When assembled, the first area 304 and the second area 306 are sealed or fluidly isolated from each other within the PCB assembly 200. The back PCB 204 defines, within the first area 304, a vent aperture or vent hole 308 that fluidly couples the back side of the diaphragm 300 to atmospheric pressure, hence defining the atmospheric side of the diaphragm 300. In the example of FIG. 3, the back PCB 204 defines three vent holes associated with the first area 304, but one or more may be used. The back PCB 204 further defines, within the second area 306, a vent aperture or vent hole 310 that fluidly couples the back side of the diaphragm 302 to atmospheric pressure, hence defining the atmospheric side of the diaphragm 302. In the example of FIG. 3, the back PCB 204 defines three vent holes associated with the second area 306, but one or more may be used, and having the same number of vent holes as between the first and second areas 304 and 306 is not required.

Considering pressure sensor 128 as representative. When the PCB assembly 200 is itself assembled and used within the conserver 106, a pressure below atmospheric pressure applied to the patient side (i.e., the visible side in FIG. 3) of the diaphragm 300 moves or flexes the diaphragm 300 toward the antenna 212. The interrogating AC signal applied to the metalized side of the diaphragm 300 (e.g., the atmospheric side, not visible) induces a responsive AC signal on the antenna 212. A pressure above atmospheric pressure (e.g., during exhalation) applied to the patient side of the diaphragm 300 moves or flexes the diaphragm 300 away from the antenna 212. The interrogating AC signal applied to the metalized side of the diaphragm 300 again induces a responsive AC signal on the antenna 212. Given the relative distances between the diaphragm 300 and the antenna 212, in the example arrangement the signal strength of the responsive AC signal induced on the antenna 212 is greater during inhalation than during exhalation. Stated otherwise, the peak-to-peak voltage of the responsive AC signal induced on the antenna 212 is greater during inhalation than during exhalation. As the diaphragm 300 moves toward the antenna 212, the peak-to-peak voltage of the responsive AC signal increases. As the diaphragm 300 moves away from the antenna 212, the peak-to-peak voltage of the responsive AC signal decreases.

In example systems, the diaphragms 300 and 302 thus move or flex toward the front PCB 202 when applied pressure is below atmospheric pressure, and move or flex toward the back PCB 204 when applied pressure is above atmospheric pressure. However, in some cases the movement toward the back PCB 204 may be limited. In particular, the distance between the atmospheric side of the diaphragms 300 and 302 and the respective areas 304 and 306 may be designed and constructed to limit movement or flexing of the diaphragms. Once the differential pressure across a diaphragm reaches a predetermined pressure, the diaphragm may abut or rest against its respective area 304 and 306, and thus the areas 304 and 306 may be considered platforms upon which their respective diaphragms rest at certain times. Similarly, in some cases the movement toward the front PCB 202 may be limited. In particular, the distance between the patient side of the diaphragms 300 and 302 and respective areas on the inside surface of the front PCB 202 may be designed and constructed to limit movement or flexing of the diaphragms. Once the differential pressure across a diaphragm during inhalation reaches a predetermined pressure, the diaphragm may abut or rest against the inside surface of the front PCB 202. The example PCB assembly 200 is described in greater detail in co-owned and commonly assigned U.S. application Ser. No. 17/601,543 filed Oct. 5, 2021 titled "System, Method and Apparatus for Dynamic Oxygen Conserver with Inhalation Sensor" which application is incorporated by reference herein as if reproduced in full below.

Before getting into more specifics regarding operation of the example system, the specification now turns to a plurality of waveforms to explain various relationships between pressure and airflow during inhalation and exhalation.

Figure 4:
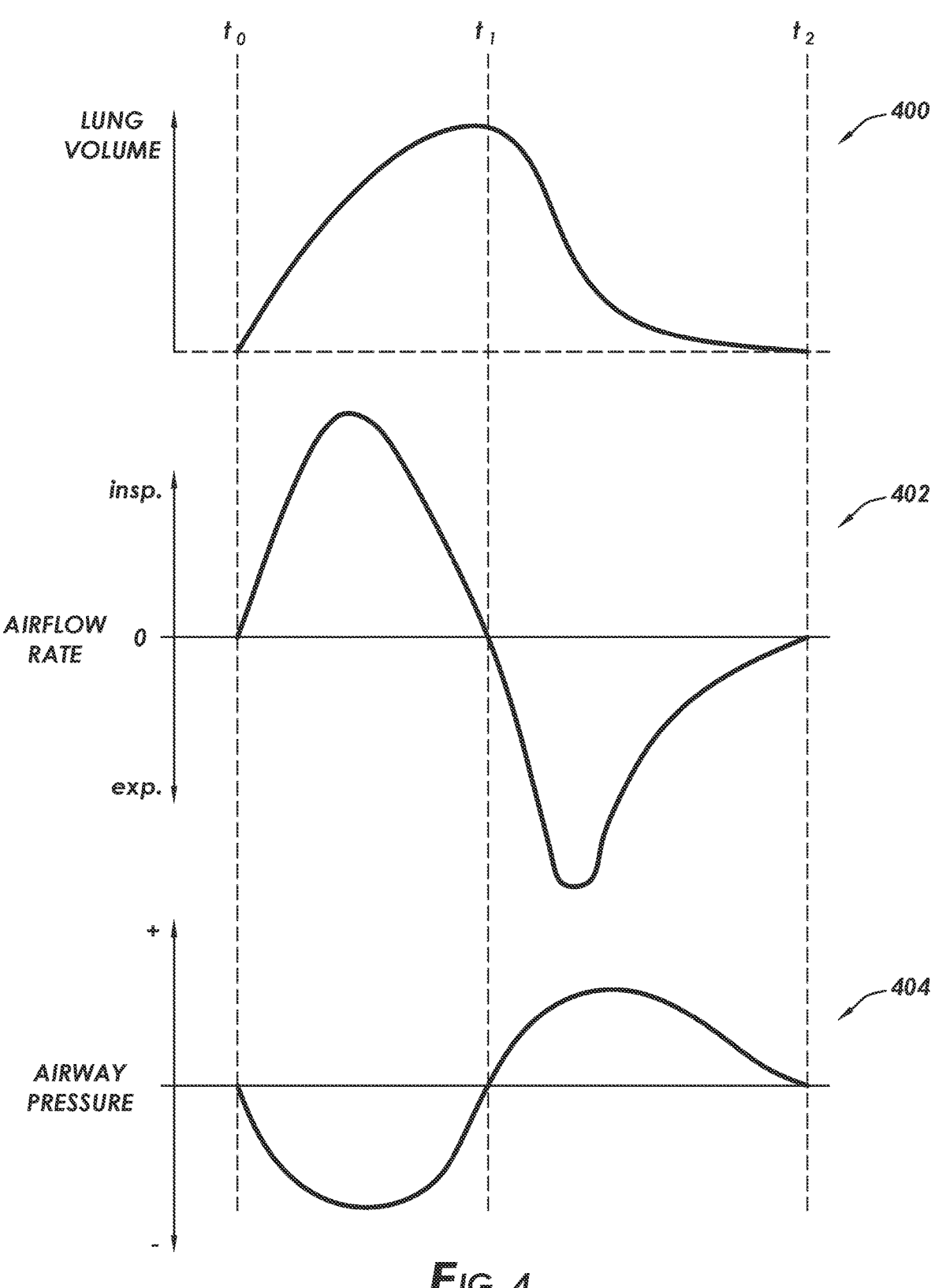
FIG. 4 shows waveforms of parameters associated with breathing, plotted on corresponding time axes.

FIG. 4 shows three waveforms plotted on corresponding time axes. In particular, FIG. 4 shows: a plot 400 of lung volume for an example inhalation followed by an exhalation; a plot 402 of airflow rate as a function of time for the example inhalation followed by the exhalation; and a plot 404 of airway pressure as a function of time for the example inhalation followed by the exhalation. Turning first to plot 400, the example breathing cycle comprises an inhalation starting at time t0 and ending time t1, immediately followed by the exhalation starting at time t1 and ending at time t2. Time t2 is also the beginning of the next inhalation, but the example waveforms end at time t2. The inhalation between t0 and t1 results in increasing volume of air held within lungs. A finite volume of air remains in the lungs just before time t0, and thus the plot 400 of lung volume does not start at zero. Lung volume of inspired air increases during the inhalation, ending at a peak volume at time t1. At time t1, the inhalation ends and the exhalation begins. As shown by the plot 400, the volume of air within the lungs falls rapidly during exhalation, and can be considered to asymptotically approach or exponential decay toward the lowest lung volume at time t2 just before the next inhalation.

Plot 402 shows rate of airflow into the lungs during the inhalation, and rate of airflow out of the lungs during exhalation. In the example plot 402, and by convention, airflow into the lungs is considered positive airflow, and airflow out of the lungs is considered negative airflow. It follows that the rate of airflow into the lungs during inhalation is plotted as positive (above zero), and the rate of airflow out of the lungs during exhalation is plotted as negative (below zero). During the example inhalation between times t0 and t1, the rate of airflow into the lungs peaks about one-half of the way through the inhalation, and then the airflow rate falls from the peak back to zero at the end of the inhalation at t1. During the example exhalation between times t1 and t2, the rate of exhalation airflow reaches a (negative) peak, and then can be considered to asymptotically approach or follow an exponential decay back toward the zero airflow rate at time t2.

Plot 404 shows airway pressure as a function of time for the example inhalation followed by the exhalation. For purposes of explanation, plot 404 may be considered to be an example waveform associated with any one of the breathing orifices open to airflow. For example, plot 404 may be a plot of pressure as a function of time associated with the right naris, the left naris, or the mouth. Regardless, each breathing orifice open to airflow has a plot similar to plot 404, differing in scale based on the amount of airflow carried by the respective breathing orifice. Again by convention, pressure associated with inhalation is considered negative (i.e., pressure lower than atmospheric pressure to draw air into the lungs), and pressure associated with exhalation is considered positive (i.e., pressure higher than atmospheric pressure to force air out of the lungs). During the example inhalation between times t0 and t1, the pressure has a sinusoidal shape starting at zero PSIG, peaking about halfway through the inhalation, and then returning the zero PSIG. During the example exhalation between times t1 and t2, the sensed pressure has a somewhat sinusoidal shape starting at zero PSIG, peaking early in the exhalation, and then returning to zero PSIG.

Figure 5:
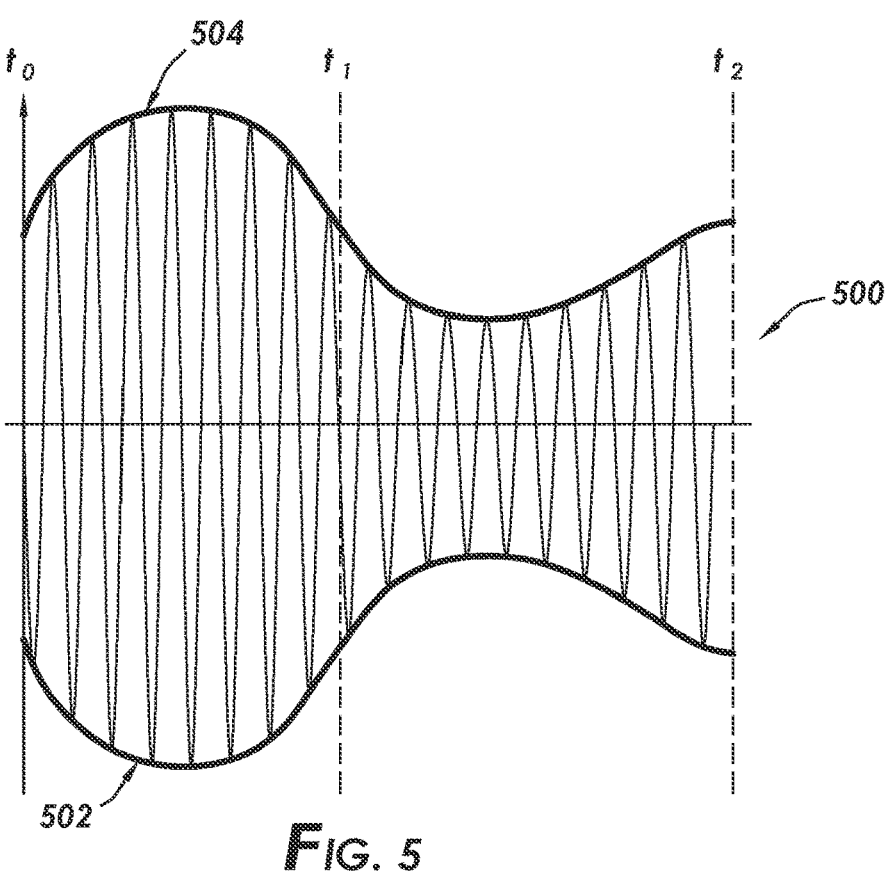
FIG. 5 shows an example waveform created by a pressure sensor responsive to the example inhalation and exhalation of FIG. 4, and in accordance with at least some embodiments.

In example systems, each pressure sensor 128 and 130 (FIG. 1) senses, in effect, a pressure waveform similar to the plot 404. However, the pressure sensors 128 and 130 do not directly recreate the waveform of plot 404. Rather, each pressure sensor 128 and 130 creates a responsive AC signal whose envelope may trace out a waveform similar to the plot 404. FIG. 5 shows an example waveform created by an ideal pressure sensor responsive to the example inhalation and exhalation of FIG. 4. In example embodiments, the interrogating AC signal may have a frequency of about 50 kilohertz (kHz), and thus the responsive AC signal 500 has the same frequency but with peak-to-peak voltage varying as a function of location of a diaphragm relative to its antenna. As shown, the peak-to-peak voltage of the responsive AC signal 500 varies over time based on the breathing cycle of the patient. During the example inhalation between times t0 and t1, followed by the exhalation between times t1 and t2, the peak-to-peak voltage of the responsive AC signal 500 varies with airway pressure. The negative peaks of the responsive AC signal 500 trace out an envelope signal or envelope 502 that reproduces (with a negative DC bias) the plot 404 of FIG. 4. Oppositely, the positive peaks of the responsive AC signal 500 trace out an inverted envelope signal or envelope 504 that reproduces (with a positive DC bias) an inverted version of the plot 404 of FIG. 4. In example cases then, the pressure waveform of plot 404 may be extracted, either directly or in inverted form, from the responsive AC signal 500.

The waveform of FIG. 5 represents a waveform that may be created by an ideal pressure sensor responsive to the full range of pressures spanning an inhalation and exhalation. However, for purposes of bolus delivery of therapeutic gas, the controller 122 (FIG. 1) is concerned with the sensed pressure contemporaneous with the transitions between exhalation and inhalation (e.g., at times around t2). The PCB assembly 200 (FIG. 2) was described as limiting the travel of the diaphragms toward the back PCB 204 (FIG. 2) during exhalations, and in some cases limiting the travel of the diaphragms toward the front PCB 202 during inhalations. The limitations in travel distance affect the responsive AC signal.

Figure 6:
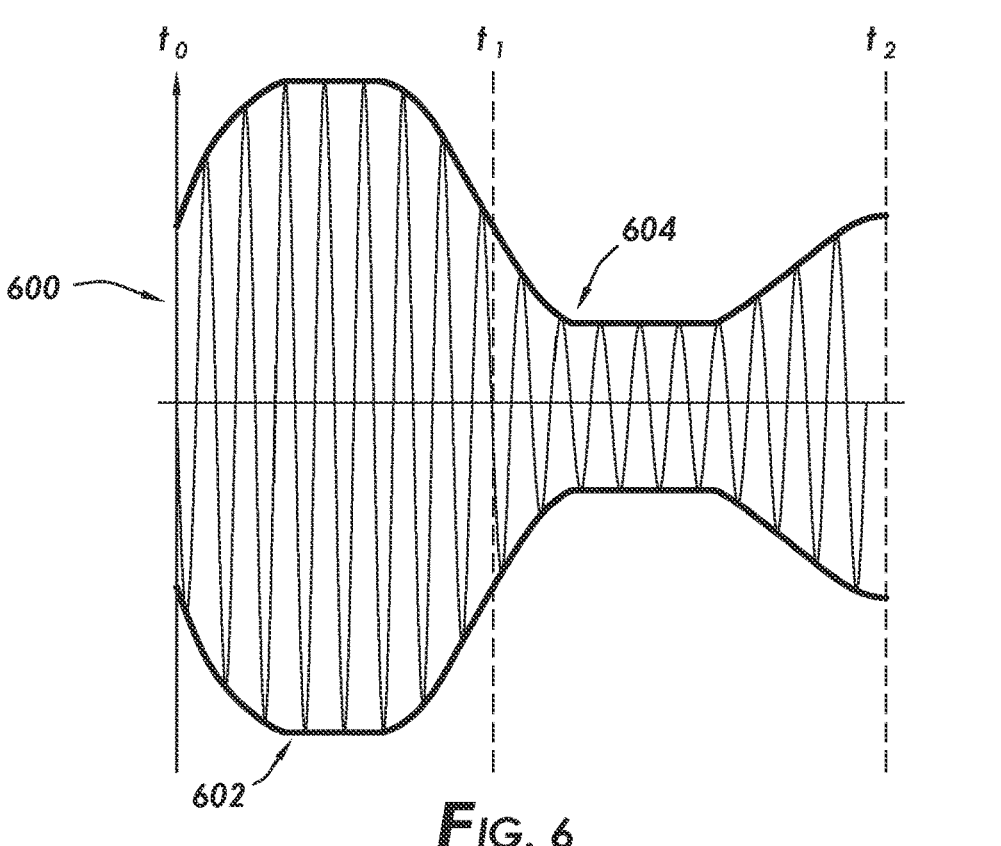
FIG. 6 shows an example waveform created by a pressure sensor responsive to the example inhalation and exhalation of FIG. 4, and in accordance with at least some embodiments.

FIG. 6 shows an example waveform created by a pressure sensor (e.g., pressure sensor 128 or pressure sensor 130) responsive to the example inhalation and exhalation of FIG. 4. As noted above, the example pressure sensors 128 and 130 may limit travel of their respective diaphragms during exhalation, which limits or clips the resultant envelopes during exhalation. Similarly, the example pressure sensors 128 and 130 may limit travel of their respective diaphragms during inhalation, which (if present) limits or clips the resultant envelopes during inhalation. As in the ideal case, the peak-to-peak voltage of the responsive AC signal 600 varies over time based on the breathing cycle of the patient. During the example inhalation between times t0 and t1, the peak-to-peak voltage of the responsive AC signal 600 varies with airway pressure, but is clipped based on the limited movement of the example diaphragm. During the example exhalation between times t1 and t2, the peak-to-peak voltage of the responsive AC signal 600 varies with airway pressure, but again is clipped based on the limited movement of the example diaphragm. The negative peaks of the responsive AC signal 600 trace out an envelope signal or envelope 602 that reproduces (with a negative DC bias) a clipped version of plot 404 of FIG. 4. Oppositely, the positive peaks of the responsive AC signal 600 trace out an inverted envelope signal or envelope 604 that reproduces (with a positive DC bias) a clipped and inverted version of the plot 404 of FIG. 4.

In practice, the interrogating AC signals may each have a frequency of about 50 kHz, and thus too the responsive AC signals 500 and 600 will have each a frequency about 50 kHz; however, a breathing cycle for an individual at rest (e.g., tidal breathing) may have a period of two or three second or more, and thus a frequency of between 0.3 Hz and 1 Hz. Thus, the example responsive AC signals 500 and 600 plotted in FIGS. 5 and 6 are not to scale in relation to the pressure waveforms; rather, the responsive AC signals 500 and 600 are presented to show how the negative peaks trace out an envelope of the pressure waveform, and how the positive peaks trace out an inverted version of the pressure waveform. Next, the clipping shown in FIG. 6 is exaggerated to show less clipping of envelopes. That is, for purposes of detecting an impending inhalation in accordance with various examples, only a small portion of the signal may be needed, and thus clipping of the exhalation may span 80% or more of the exhalation, yet there is still sufficient information to detect the upcoming inhalation from the within the exhalation.

The inventor of the current specification found that an upcoming or impending inhalation may be detected during the exhalation. In particular, during periods of time when the patient is exhaling, the airflow rate changes over time as shown by plot 402 of FIG. 4; however, the inventor of the current specification found that an abrupt change in the airflow rate (e.g., a change from the exponential decay) is present during the exhalation, and that abrupt change is indicative of an upcoming inhalation. Stated in terms of airway pressure, the inventor of the current specification found that an abrupt change in the airway pressure (e.g., a change that does not follow the exponential decay in pressure) is present, and that abrupt change is indicative of an upcoming inhalation.

Figure 7:
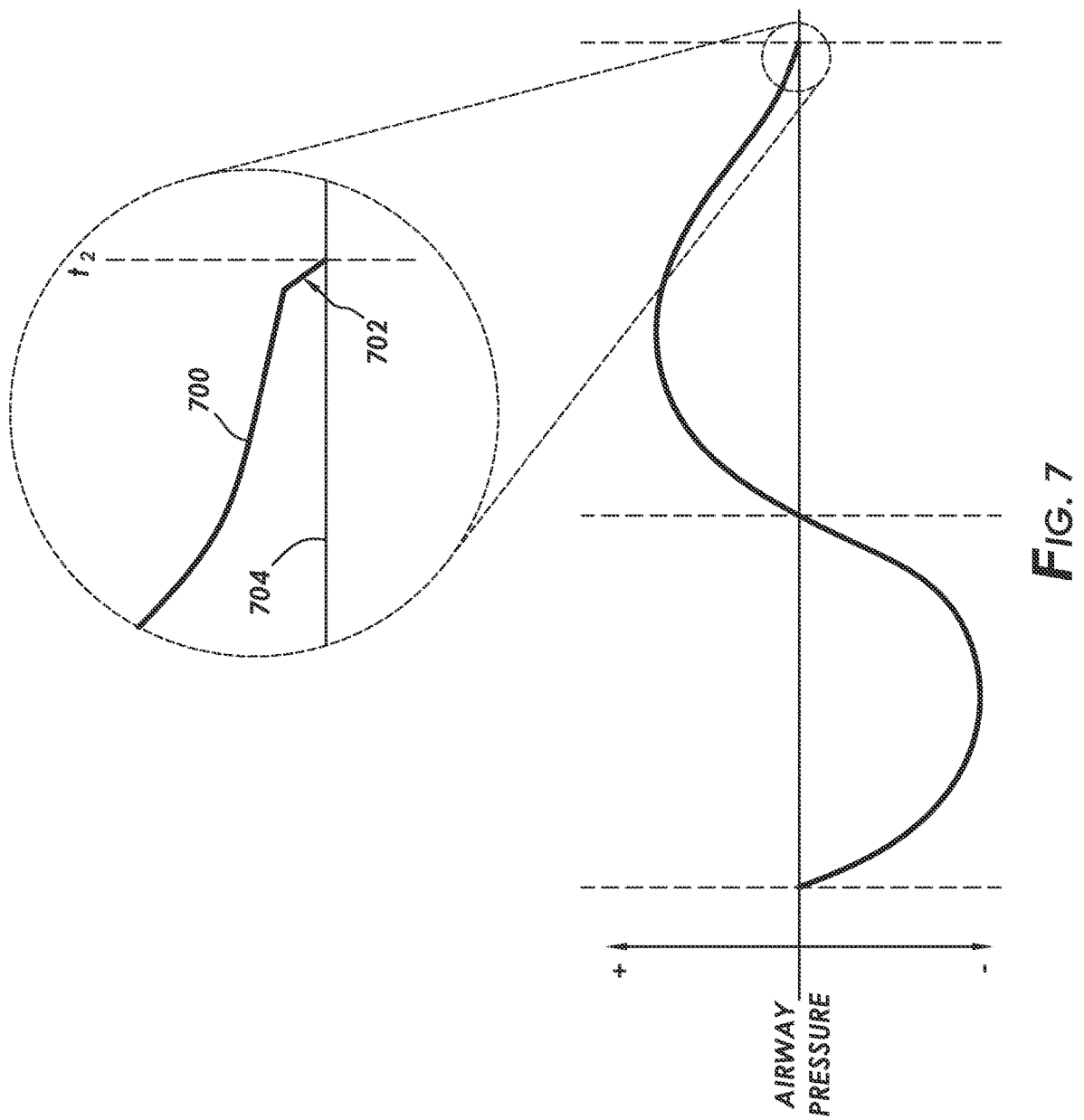
FIG. 7 shows a plot airway pressure of a breathing cycle, including a magnified portion, in accordance with at least some embodiments.

FIG. 7 shows a plot of airway pressure during a breathing cycle, including a magnified portion to show the abrupt change indicative of an impending inhalation. In particular, in the waning moments of the exhalation (e.g., 10-100 milliseconds (ms) prior to the reversal of airflow corresponding to the contiguous inhalation), the exhalation airflow exhibits a downward spike in pressure (and corresponding downward spike in airflow rate) just before the transition to a contiguous inhalation. Referring to the magnified portion of the FIG. 7, the airway pressure waveform 700 exhibits a downward spike 702 in pressure which disrupts the exponential decay and eventually results in a reversal of airflow (e.g., pressure crosses the zero line 704). The size of the spike 702 shown in FIG. 7 is exaggerated for clarity. For purposes of this specification and claims, the short spike 702 shall not be consider an inhalation because such is still exhalation airflow.

The specification now turns to possible physiological explanations for the spike 702. It will be understood that the inventor of the present specification has not, as of this writing, been able to confirm which (if any) of the possible physiological explanations are the actual cause of the spike 702. Thus, the possible physiological explanations shall not be read alone or in combination as limitations. The possible physiological explanations may be broadly categorized into: 1) actions of the patient's diaphragm; 2) actions of the secondary muscles associated with inhalation; and 3) the physiological inhalation as distinct from inhalation defined by a reversal of airflow, and correspondingly airway pressure crossing the zero point. Turning first to the patient's diaphragm.

A human diaphragm is a muscular sheet that separates the thoracic cavity from the abdominal cavity. The diaphragm is the primary muscle involved in respiration. That is, when the diaphragm contracts, the volume of the thoracic cavity increases, which creates a pressure less than atmospheric pressure to draw air into the lungs. When the diaphragm relaxes, exhalation takes place. Though it is possible to force air from the lungs (e.g., by contracting the muscles associated with the rib cage), in tidal breathing exhalation is largely a function of the change of volume of the thoracic cavity caused by relaxation of the diaphragm.

One possible explanation for the spike 702 in airway pressure (and corresponding spike in airflow rate) is the patient's diaphragm. For example, the spike 702 may be attributable to the activation of the diaphragm in preparation for the impending inhalation. For example, near the end of an exhalation the diaphragm of the patient may be "readied" by a command to tense or hold in place. That is, the initial command may cause the diaphragm to become rigid, but not yet contract for the inhalation. Thus, the spike 702 may be caused by the diaphragm tensing to hold in place, thus ending asymptotic approach of exhalation airflow toward zero and shifting toward the zero crossing.

Another possible explanation, again based on the patient's diaphragm, has to do with the speed of electrical signals traveling along nerves. The diaphragm, as a muscle, is triggered to contract by the phrenic nerve. Electrical signals traveling along nerve pathways vary in speed, ranging from 0.5 meters/second (m/s) for pain signals to about 120 m/s for muscle contraction signals. Thus, much like the finite and non-zero time it takes for electrical signals to travel around and trigger a heartbeat, the nerve signals to cause contraction of the diaphragm take a finite and non-zero amount of time to traverse the diaphragm. Consider that, in the fully relaxed state, the diaphragm has an inverted bowl shape. The phrenic nerve enters the diaphragm near the apex of the inverted bowl shape. Thus, contraction of the diaphragm starts near the apex of the bowl shape and works its way spherically down to where the diaphragm contacts the thoracic wall. Thus, another possible explanation for the spike 702 is that the apex initially tenses and flattens causing the spike 702 which reduces exhalation airflow rate and thus airway pressure, and as the nerve signal spreads spherically around the diaphragm, eventually the full inhalation begins.

Another possible explanation for the spike 702 is action of the secondary muscles that assist in inhalation, but to a lesser degree than the diaphragm, such as the sternocleidomastoids, the abdominal muscles, and/or the muscles associated with the rib cage. That is, in preparation for an inhalation, the patient's body may command the various secondary muscles to tense or become rigid. While the preparation of the secondary muscles may be below the conscience level, the tensing may cause the marked decrease in exhalation airflow associated with spike 702.

Yet another possible explanation for the spike 702 is the difference between the physiological beginning of an inhalation as compared to the physical beginning of an inhalation. That is, the point in time represented by the discontinuity in the exponential decay airway in airway pressure (and corresponding discontinuity in airflow rate) may be the point in time at which any of the primary or secondary muscles associated with inhalation begin contracting for the contiguous inhalation. The spike 702, while still the zone of exhalation airflow, thus represents the last vestiges of exhalation airflow in the transition to the contiguous inhalation airflow at time t2 when the airway pressure transitions to a pressure below atmospheric and the airflow crosses the zero point to become inhalation airflow.

The possible physiological explanations for the spike 702 are not mutually exclusive—the spike 702 may be caused by two or more of these, or interactions between them. Moreover, there may be other physiological explanations for the spike 702 not currently understood. Thus again, possible physiological explanations shall not be read as limiting the disclosure and claims.

Figure 8:
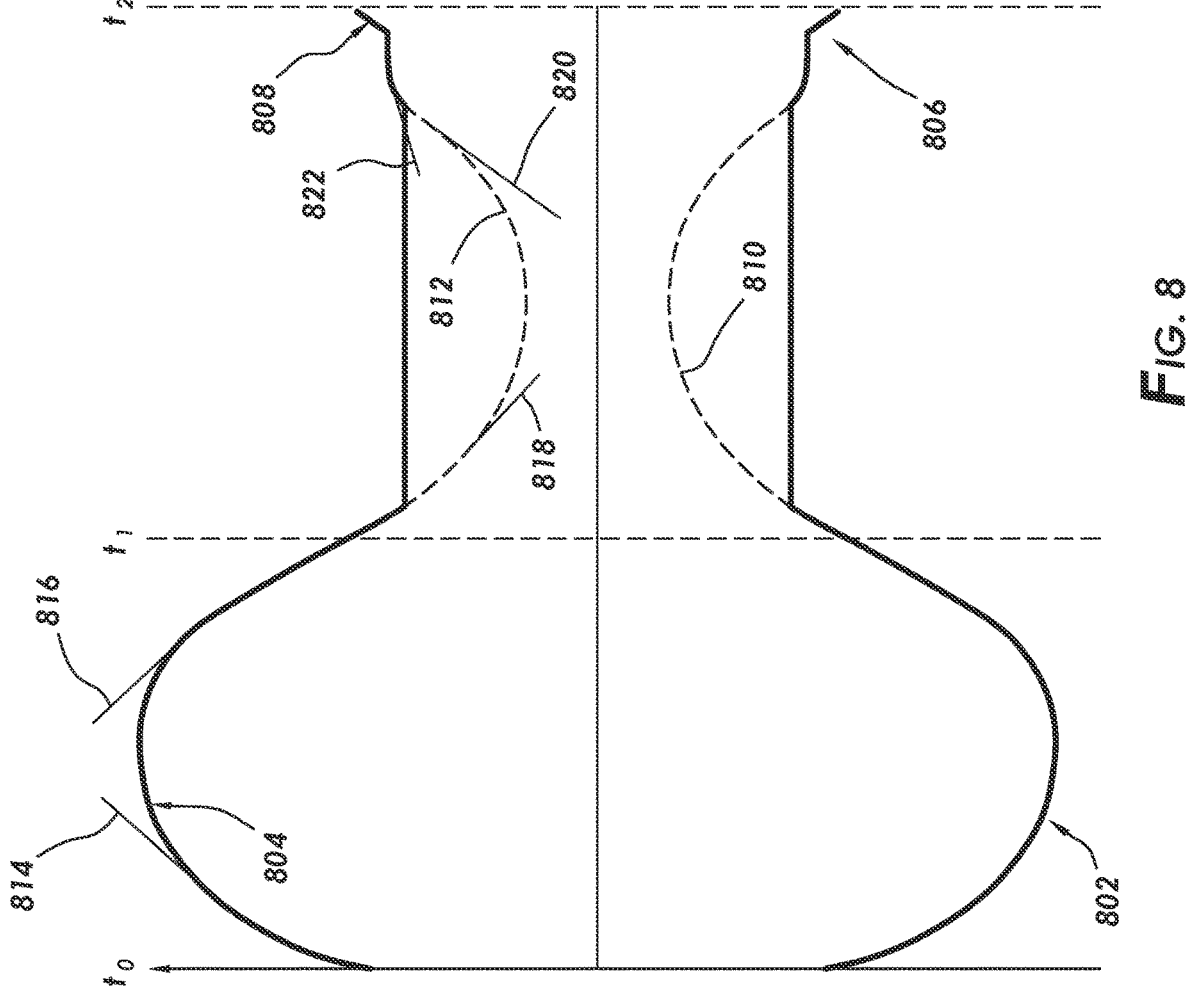
FIG. 8 shows an example set of envelopes of a waveform created by a pressure sensor responsive to the example inhalation and exhalation of FIG. 4, and in accordance with at least some embodiments.

FIG. 8 shows an example set of envelopes of a waveform created by a pressure sensor responsive to the example inhalation and exhalation of FIG. 4. In particular, FIG. 8 shows envelope 802 associated with the negative peaks of a responsive AC signal, and shows envelope 804 associated with the positive peaks of the responsive AC signal. FIG. 8 does not reproduced an example responsive AC signal so as not to unduly complicate the figure; however, it will be understood that the envelopes 802 and 804 are based on such a responsive AC signal. Further, FIG. 8 shows clipping of the responsive AC signal during the exhalation, which clipping may be caused by the diaphragm of the pressure sensor resting on or abutting the back PCB 204 (FIG. 2) during the exhalation. In this case, however, the clipping is more prominent than that shown in FIG. 6. Nevertheless, for purposes of explanation the unclipped portion of the exhalation airflow is shown as dashed line 810 for the negative peaks and dashed line 812 for the positive peaks. Finally, FIG. 8 shows a spike 806 associated with the envelope 802, and a counterpart spike 808 associated with the envelope 804, both spikes being a manifestation of the spike 702 (FIG. 7) and both spikes exaggerated for purposes of discussion.

Referring to the envelope 804. Again, the envelope 804 can be considered an inverted version of the airway pressure waveform shown by plot 404 (FIG. 4) and having a positive DC bias. A line tangent to the envelope 804 at any point in time is representative of airflow rate at that point in time. Stated otherwise, a first derivative of the envelope 804 at a point in time is representative of airflow rate at that point in time. For example, line 814 shows an airflow rate a point in time when airflow is increasing during the inhalation, and line 816 shows an airflow rate a point in time when airflow is decreasing during the inhalation. During the exhalation, similar tangent lines and/or first derivatives are indicative of the airflow rate. For example, line 818 shows an airflow rate in an early portion of the exhalation, line 820 shows an airflow rate in the second one-half of the exhalation, and line 822 shows the airflow rate just before the spike 808. Considered in terms of slope of the tangent lines, the slopes as between lines 820 and 822 are trending toward zero or declining. Considered in terms of first derivatives, the first derivatives as between lines 820 and 822 are trending toward zero or declining—the waning rate is trending toward zero or declining. The spike 808 (based on spike 702) represents a change in the airflow rate prior to the contiguous inhalation (beginning at time t2), and in particular represents an abrupt decrease in the airflow rate. Considered in terms of slope of tangent lines, a line tangent to the spike 808 represents an increased slope compared to the slopes represented by lines 820 and 822. It follows the spike 808 represents a reversal of the trend of the slopes of the tangent lines and/or first derivatives associated with the envelope 804. Stated in terms of airflow rate, the spike 808 represent a shoulder or discontinuity in the exhalation airflow rate. A similar description may be presented with the respect to the envelope 802, but with the slopes reversed.

Thus, example embodiments sense the change in airflow in the form of the spike 808—such as sensing a shoulder or discontinuity in the airflow rate or sensing a change in the trend of the slopes of the airway pressure. Stated another way, example embodiments detect a change in the trend of the airway pressure from trending toward zero (e.g., smooth transition from the slope of line 820 to the slope of line 822), the example change being a reversal of the trend of the slopes toward zero at the contiguous inhalation—all during the exhalation airflow.

In example embodiments, the clipping caused by the diaphragms abutting the back PCB 204 (FIG. 2) during exhalation may enable or enhance the ability of the conserver 106 to sense the spike 702 (FIG. 7). In particular, the inventor of the present specification believes that limiting the flexing or bending of the diaphragms of the pressure sensors in the exhalation direction enhances the detectability of the spike 702. Consider again FIG. 5 showing a responsive AC signal 500 from an ideal pressure sensor that does not limit travel of the diaphragm. As the airway pressure during the exhalation trends toward zero, an unconstrained diaphragm of such a pressure sensor begins movement back toward a neutral position from a maximum deflection. To the extent a pressure spike occurs during the exhalation, movement of the diaphragm toward the receiving antenna responsive to the pressure spike causes a change in the responsive AC signal, but because the diaphragm of the pressure is still relatively far from the antenna, the change in the responsive AC signal may be small. Returning to FIG. 8, by contrast, in example pressure sensors where the flexing or bending of the diaphragms is limited in the exhalation direction, assuming the pressure spike causes the same displacement as the non-constrained case, because the diaphragm of the pressure is closer to the antenna, the change in the responsive signal is more pronounced.

Thus, the inventor of the present specification believes that limiting movement or flexing of the diaphragm in the exhalation direction may increase signal strength of the responsible AC signal with respect to the pressure spike.

Stated otherwise, having the diaphragm abut the back PCB 204 (FIG. 2) during a portion of the exhalation may increase the sensitivity of the pressure sensor to the pressure spike 702 (FIG. 7), enabling detection of the pressure spike 702 as the mechanism to trigger bolus delivery to the patient 110 (FIG. 1). Though the trigger may occur during the exhalation, time delay associated with operation of the controller 122 (e.g., 10 to 20 ms), and the finite amount of time for the bolus to travel from the conserver 106 to the patient 110 along the nasal cannula, the bolus of therapeutic gas may arrive at the breathing orifice earlier in the inhalation that related-art systems and methods. The inventor of current specification further believes that, as the accuracy and responsiveness of sensors (e.g., pressure sensors, flow sensors) improves over time, such improved sensors may directly detect the pressure spikes, and thus using a diaphragm sensor with a diaphragm having limited travel in the exhalation direction shall not be read as a requirement in the various claimed systems and methods.

Figure 9:
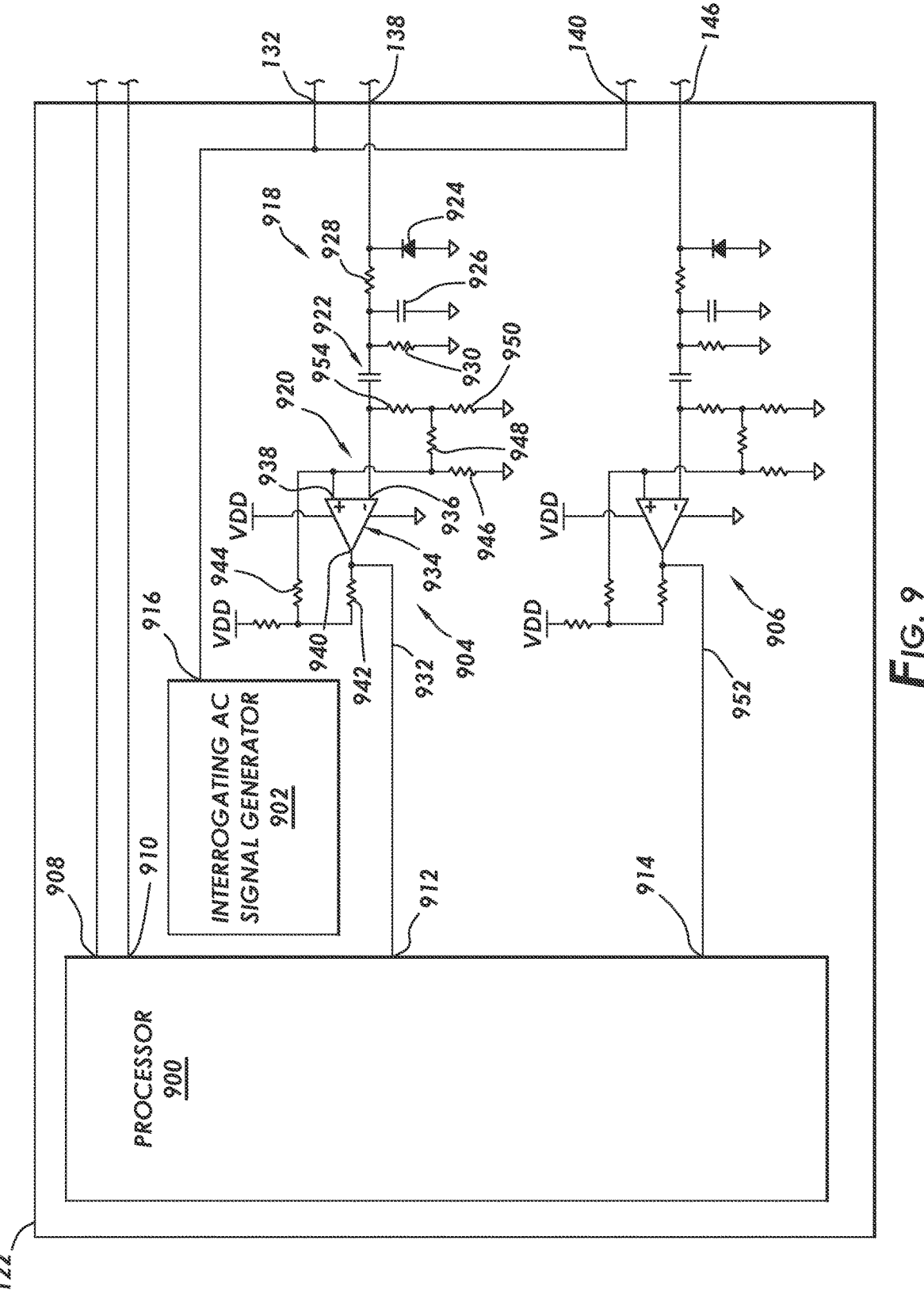
FIG. 9 shows an electrical block diagram of a controller in accordance with at least some embodiments.

FIG. 9 shows a block diagram of a controller 122. In particular, the example controller 122 defines a processor 900, and interrogating AC signal generator 902, a right-naris signal detector 904, and a left-naris signal detector 906. The example processor 900 defines a drive output 908 coupled to the two-port valve 124 (FIG. 1) and a drive output 910 coupled to the two-port valve 126 (FIG. 1). By asserting the drive outputs 908 and/or 910, the processor 900 may control the delivery of a bolus of therapeutic gas to the patient 110 (FIG. 1). Though not specifically show, each of the drive outputs 908 and 910 may be associated with a driver circuit to provide voltage and current to the solenoid or other control mechanisms of the two-port valves. The example processor 900 further defines a right-naris sense input 912 and a left-naris sense input 914. By way of the 700 and 914, the processor 900 may receive binary or Boolean indications of an impending inhalation of the patient (e.g., assertion of such signals indicating the detection of a spike 702 (FIG. 7)) or an actual inhalation). The processor 900 may take any suitable form, such as an ASIC, a microcontroller with controlling software, DSP with controlling software, a PLD with controlling software, a PSOC, or an FPGA. In yet still further cases, the functionality of the processor 900 may be implemented by discrete electrical components.

The interrogating AC signal generator 902 defines a signal output 916 upon which is driven the interrogating AC signal. In example cases, the signal output 916 is coupled to and defines the signal output 132 and signal output 140. In other cases, there may be a separate signal generated for each of the signal outputs 132 and 140. In example cases, the interrogating AC signal generator 902 generates the interrogating AC signal in the form a 50 kHz AC signal having a peak-to-peak voltage of about 5 Volts, but other frequencies (e.g., between and including 20 kHz and 100 kHz) and other peak-to-peak voltages (e.g., between and including 3.3V and 24V) may be used.

In example systems, the right-naris signal detector 904 and the left-naris signal detector 906 are duplicative or identical circuits associated one each with the pressure sensor 128 and pressure sensor 130, respectively. In other cases, however, the right-naris signal detector 904 may be arranged and operated differently from the left-naris signal detector 906 (e.g., slightly different trigger points) if such provides an operational advantage. Referring to the right-naris signal detector 904 as representative, the right-naris signal detector 904 may be conceptually, though not necessarily physically, divided into an envelope detector 918 and a level detector 920 separated by a DC blocking capacitor 922. Each is address in turn.

The example envelope detector 918 comprises a rectifier in the example form a diode 924 in combination with a low-pass filter in the example form of a capacitor 926 and resistors 928 and 930. In particular, the cathode of diode 924 is coupled to and defines the sense input 138, and the anode is coupled to a reference voltage (e.g., common or ground). The responsive AC signal applied to the sense input 138 is thus rectified by the diode 924. In particular, for instantaneous voltage of the responsive AC signal above about −0.7V (i.e., when the voltage across the diode is less than about 0.7 V), the responsive AC signal is passed to the low-pass filter. For instantaneous voltage of the responsive AC signal below about −0.7V, the example diode 924 becomes conductive and clips or limits the further negative voltages applied to the downstream components. In other cases, the anode of the diode 924 may couple to and define the sense input 138, and thus the diode 924 may more directly rectify the incoming responsive AC signal.

The rectified AC signal created by the diode (in any suitable configuration) is passed to the low-pass filter in the example form of the capacitor 926 and the resistors 928 and 930. In particular, in the example system the resistor 928 has a first lead coupled to receive the rectified AC signal (here, coupled to the cathode of diode 924), and a second lead coupled to the first lead of the capacitor 926. The second lead of the capacitor 926 is coupled to the reference voltage (e.g., common or ground). In example systems, the resistor 928 and capacitor 926 are selected to implement a low-pass filter having a cut-off frequency of less than 20 Hz, in some case less than 15 Hz, and in a particular example about 11 Hz. Resistor 930 has a first lead coupled to the node between the resistor 928 and the capacitor 926, and a second lead coupled to the reference voltage. The resistor 930 has a resistance (e.g., about 1 mega-Ohm) selected to bleed off the charge stored on the capacitor 926. The arrangement of the rectifier and the low-pass filter implement the envelope detector 918 designed and constructed to extract the envelope created by the positive peaks of responsive AC signal (e.g., envelope 504, envelope 604, or envelop 804). The detected envelope is then passed to the DC blocking capacitor 922.

Still referring to FIG. 9, and the representative right-naris signal detector, the DC blocking capacitor 922 has a first lead coupled to the node between the resistor 928 and the capacitor 926, and a second lead coupled to the level detector 920. As the name implies, the DC blocking capacitor is designed and constructed to block DC bias of the detected envelope. In the example case of detecting the envelope based on the positive peaks of the responsive AC signal, the DC blocking capacitor blocks the positive DC bias, and thus the passes the inverted version of the airway pressure waveform to the level detector 920.

The example level detector 920 is coupled to the second lead of the DC blocking capacitor 922, and defines detector output 932 coupled to the right-naris sense input 912. The example level detector 920 is designed and constructed to receive the envelope depicting the (inverted) airway pressure waveform, and sense, during the exhalation, a change in signal level indicative of presence of the spike 702 (e.g., pressure spike 808). When the change in signal level indicative of spike 702 is detected, the example level detector 920 asserts the detector output 932 (e.g., in the example circuit, asserted low). To that end, the example level detector 920 implements an operational amplifier 934 defining an inverting input 936 coupled to the second lead of the DC blocking capacitor, a non-inverting input 938, and a compare output 940 coupled to and defining the detector output 932. The example level detector 920 may implement hysteresis by varying the magnitude of the trigger reference applied to the non-inverting input 938. For example resistors 942, 944, and the voltage divider implemented by resistors 946, 948, and 950, implement different trigger references applied to the non-inverting input 938 depending on the asserted or non-asserted state of the compare output 940. In one example arrangement, when the compare output 940 has a high voltage (e.g., VDD), the trigger reference created and applied to the non-inverting input 938 has an upper level (e.g., about 2.5V for a VDD of 3.3V). Further in the example arrangement, when the compare output 940 has a low voltage (e.g., common or ground), the trigger reference created and applied to the non-inverting input 938 has a lower level (e.g., about 1.5V for a VDD of 3.3V).

In such a configuration, as an exhalation begins the compare output 940 is non-asserted (here, having a higher voltage), and thus the trigger reference has the higher level. Once the spike (or an inhalation in the absence of the spike) passes the DC blocking capacitor 922, the voltage at the inverting input 936 rises above the upper level. Once the voltage at the inverting input 936 rises above the upper level, the operational amplifier 934 asserts the compare output 940 (here, asserted low). The low voltage on the compare output 940 changes the trigger reference applied to the non-inverting input to the lower voltage, and thus the level detector 920 implements the hysteresis. That is, once the signal applied to the inverting input 936 rises above the upper trigger level, the compare output 940 is asserted and the lower level trigger reference is applied, ensuring that the compare output 940 stays asserted for a sufficient period of time to be detected by the processor 900.

In some examples, and as shown, additional though slight modifications to the trigger reference may also be implemented by the level detector 920 responsive to the envelope passing through the DC blocking capacitor 922. In particular, resistor 954 has a first lead coupled to the downstream side of DC blocking capacitor 922, and a second lead coupled to the node between resistors 948 and 950. As the envelope passes through the DC blocking capacitor 922, increasing magnitude of the envelope increases the trigger reference applied to the non-inverting input 938, and vice versa. In example implementations, the resistor 954 has a relatively high value (e.g., 2.2 mega-Ohms), and thus the contribution is relatively small, but nevertheless contributes to the hysteresis implemented by the level detector 920. In other cases, the resistor 954 may be omitted.

The example left-naris signal detector 906 is duplicative of or identical to the right-naris signal detector 904, and thus will not be described in detail so as not to unduly lengthen the specification. Suffice it say that the left-naris signal detector 906 defines the sense input 146, and asserts a detector output 952 (coupled to the left-naris sense input 914) when a spike or actual inhalation is detected. And similarly, the left-naris signal detector may implement hysteresis by way of dual trigger-levels applied to the operational amplifier.

As implied by the FIG. 9, the example embodiments utilize analog circuits to detect the spike 702 (and its manifestations in the form of spikes 806 or 808). In some, but not necessarily all, cases an analog detection may be implemented because the time width of the spike 702 (i.e., the time duration between the discontinuity or shoulder and the change of direction of airflow) may be shorter than the sampling period of the digital inputs implemented by the processor 900. That is, while theoretically possible to couple the responsive AC signal, or the envelope signal created by the envelope detector 918, directly to an analog input (not specifically shown) of the processor 900, the processor 900 only periodically samples such analog inputs. If the sampling period is longer than the time width of the spike 702, the processor 900 may be unable to consistently (i.e., breath to breath) detect the spike 702. However, as processing technology advances (e.g., stand-alone processors, micro-controllers), the sample rate of analog inputs may improve such that the analog signal detectors may be omitted. Thus, the example use of analog circuits detecting the pressure spikes asserting Boolean signals to a downstream processor shall not be read as a limitation of the invention.

The various embodiments discussed to this point operate on the envelope 804 (FIG. 8) created by the positive peaks of the responsive AC signal, and thus operate on an inverted version of the pressure waveform. However, one having ordinary skill in the art, with the benefit of this disclosure, could now design equivalent circuits to operate based on the envelope 802 (FIG. 8) created by the negative peaks of the responsive AC signal, and thus operate on a non-inverted version of the pressure waveform. Thus, the example circuits, operating on the envelope 804 created by the positive peaks of the responsive AC signal, shall not be read as a limitation.

Figure 10:
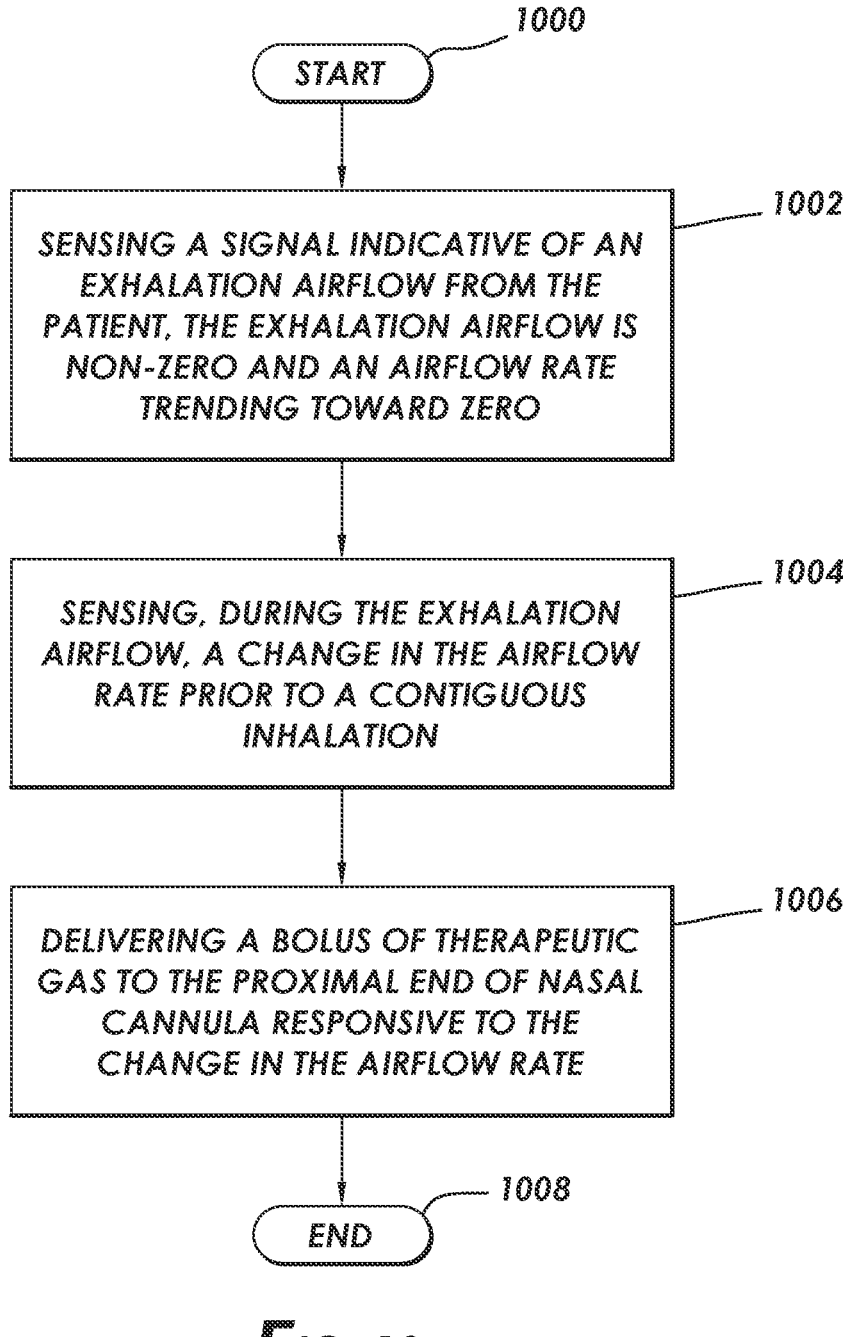
FIG. 10 shows a method in accordance with at least some embodiments.

FIG. 10 shows a method in accordance with at least some embodiments. In particular, the method starts (block 1000) and comprises providing therapeutic gas to a patient by: sensing a signal indicative of an exhalation airflow from the patient, the exhalation airflow is non-zero and an airflow rate trending toward zero (bock 1002); sensing, during the exhalation airflow, a change in the airflow rate prior to a contiguous inhalation (block 1004); and delivering a bolus of therapeutic gas to the proximal end of nasal cannula responsive to the change in the airflow rate (block 1006). Thereafter, the method ends (block 1008), likely to be restarted relative to the next inhalation.

The above discussion is meant to be illustrative of the principles and various embodiments of the present invention. Numerous variations and modifications will become apparent to those skilled in the art once the above disclosure is fully appreciated. For example, while the example conserver 106 is shown to be operational with respect to the nares of the patient, in yet still further cases the conserver 106 may additional be sensitive to breathing through the mouth. In such cases, the conserver 106 may have an additional sensor (e.g., an additional pressure sensor or flow sensor), and an additional signal detector, but otherwise operation is similar to operation with respect the nares as discussed herein. It is intended that the following claims be interpreted to embrace all such variations and modifications.

What is claimed is:

1. A method of providing therapeutic gas to a patient, the method comprising:
   sensing a signal indicative of an exhalation airflow from the patient, the exhalation airflow is non-zero and an airflow rate trending toward zero;
   sensing, during the exhalation airflow, a change in the airflow rate prior to a contiguous inhalation; and
   delivering a bolus of therapeutic gas to a proximal end of nasal cannula responsive to the change in the airflow rate.

2. The method of claim 1 wherein sensing the signal indicative of the exhalation airflow further comprises sensing air pressure over time, the air pressure over time indicative of the exhalation airflow.

3. The method of claim 1 wherein sensing the change in the airflow rate further comprises sensing a decrease in the airflow rate.

4. The method of claim 1:
   wherein sensing the signal indicative of the exhalation airflow further comprises receiving a responsive AC signal from a diaphragm of a diaphragm sensor, the diaphragm of the diaphragm sensor abutting a platform that limits movement of the diaphragm during at least a portion of the exhalation airflow; and
   wherein sensing the change in the airflow rate further comprises sensing a change in magnitude of an envelope defined by the responsive AC signal from the diaphragm sensor.

5. The method of claim 4 wherein sensing the change in magnitude of the envelope defined by the responsive AC signal from the diaphragm sensor further comprises sensing a change in magnitude of an envelope defined by peaks of the responsive AC signal.

6. The method of claim 4 wherein delivering the bolus of therapeutic gas further comprises delivering the bolus of therapeutic gas responsive to the envelope having a magnitude rising through a trigger reference.

7. A therapeutic gas delivery device comprising:
   a controller;
   a first sensor electrically coupled to the controller and fluidly coupled to a first-hose connection, the first sensor configured to create a first signal indicative of airflow through the first-hose connection;
   a first valve electrically coupled to the controller and configured to fluidly coupled a source-hose connection to the first-hose connection; and
   the controller is configured to:
      sense, by way of the first signal indicative of airflow, exhalation airflow associated with the first-hose connection, the exhalation airflow having an airflow rate, and the airflow rate trending toward zero at a waning rate;
      sense, during the exhalation airflow, a change in the waning rate, the change prior to a contiguous inhalation; and
      command the first valve to couple the source-hose connection to the first-hose connection to deliver a bolus of therapeutic gas, the command responsive to the change in the waning rate.

8. The therapeutic gas delivery device of claim 7 further comprising:
   a second sensor electrically coupled to the controller and fluidly coupled to a second-hose connection, the second sensor configured to create a second signal indicative of airflow of through the second-hose connection;
   a second valve electrically coupled to the controller and configured to fluidly couple the source-hose connection to the second-hose connection; and
   when the controller senses exhalation airflow, the controller is further configured to sense by way of the first signal indicative of airflow and the second signal indicative of airflow.

9. The therapeutic gas delivery device of claim 8 wherein the controller is further configured to command the second valve to couple the source-hose connection to the second-hose connection responsive to the change in the waning rate.

10. The therapeutic gas delivery device of claim 7 wherein the first sensor further comprises a first pressure sensor associated with the first-hose connection.

11. The therapeutic gas delivery device of claim 7:

wherein the first sensor further comprises a diaphragm sensor comprising a diaphragm;

wherein the controller is further configured to receive a responsive AC signal from the diaphragm of the diaphragm sensor, the diaphragm abutting a platform that limits movement of the diaphragm in an exhalation direction for at least a portion of the exhalation; and wherein when the controller senses the change in the waning rate, the controller is further configured to sense the change in magnitude of an envelope defined by the responsive AC signal from the diaphragm sensor.

12. The therapeutic gas delivery device of claim 11 wherein when the controller senses the change in magnitude of the envelope defined by the AC responsive signal from the diaphragm sensor, the controller is further configured to sense the change in magnitude of the envelope defined by peaks of the AC responsive signal from the diaphragm sensor.

13. The therapeutic gas delivery device of claim 11 wherein when the controller commands the first valve to deliver the bolus of therapeutic gas, the controller is further configured to deliver the bolus of therapeutic gas responsive to the envelope having a magnitude rising through a trigger reference.

14. A therapeutic gas delivery device comprising:

a controller;

a first sensor electrically coupled to the controller and fluidly coupled to a first-hose connection, the first sensor configured to create a first signal indicative of airflow associated with the first-hose connection;

a first valve electrically coupled to the controller and configured to fluidly coupled a source-hose connection to the first-hose connection;

a second sensor electrically coupled to the controller and fluidly coupled to a second-hose connection, the second sensor configured to create a second signal indicative of airflow of associated with the second-hose connection;

a second valve electrically coupled to the controller and configured to fluidly couple the source-hose connection to the second-hose connection;

the controller is configured to:

read the first signal indicative of airflow;

read the second signal indicative of airflow;

sense, based on the reading, exhalation associated with the first-hose connection or the second-hose connection, the exhalation having an airflow rate, and the airflow rate declining over time;

sense, during the exhalation, an increase in the airflow rate, the increase in the airflow rate prior to a contiguous inhalation; and command the first valve to couple the source-hose connection to the first-hose connection to deliver a bolus of therapeutic gas, the command responsive to the increase in the airflow rate.

15. The therapeutic gas delivery device further of claim 14 wherein the controller is further configured to command the second valve to couple the source-hose connection to the second-hose connection responsive to the increase in airflow rate.

16. The therapeutic gas delivery device of claim 14:

wherein the first sensor further comprises a first pressure sensor associated with the first-hose connection;

wherein the second sensor further comprises a second pressure sensor associated with the second-hose connection.

17. The therapeutic gas delivery device of claim 14:

wherein the first sensor further comprises a diaphragm sensor comprising a diaphragm;

wherein when the controller reads the first signal indicative of airflow, the controller is further configured to receive a responsive AC signal from the diaphragm of the diaphragm sensor; and wherein when the controller senses the increase in the airflow rate, the controller is further configured to sense a change in magnitude of an envelope defined by the responsive AC signal from the diaphragm sensor.

18. The therapeutic gas delivery device of claim 17 wherein when the controller senses the change in magnitude of the envelope defined by the responsive AC signal from the diaphragm sensor, the controller is further configured to sense the change in magnitude of the envelope defined by peaks of the responsive AC signal from the diaphragm sensor.

* * * * *